(12) United States Patent
Ryu et al.

(10) Patent No.: US 11,827,912 B2
(45) Date of Patent: Nov. 28, 2023

(54) **CHIMERIC ENDOLYSIN LYS109 WITH ANTIMICROBIAL ACTIVITY AGAINST *STAPHYLOCOCCUS AUREUS***

(71) Applicant: SEOUL NATIONAL UNIVERSITY R&DB FOUNDATION, Seoul (KR)

(72) Inventors: Sangryeol Ryu, Seoul (KR); Bokyung Son, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 104 days.

(21) Appl. No.: 17/618,121

(22) PCT Filed: Apr. 21, 2020

(86) PCT No.: PCT/KR2020/005243
§ 371 (c)(1),
(2) Date: Dec. 10, 2021

(87) PCT Pub. No.: WO2020/256268
PCT Pub. Date: Dec. 24, 2020

(65) Prior Publication Data
US 2022/0228135 A1 Jul. 21, 2022

(30) Foreign Application Priority Data
Jun. 19, 2019 (KR) .................... 10-2019-0073058

(51) Int. Cl.
  *C12N 9/36* (2006.01)
  *A61K 38/47* (2006.01)
  *C11D 3/386* (2006.01)

(52) U.S. Cl.
  CPC ............ *C12N 9/2462* (2013.01); *A61K 38/47* (2013.01); *C11D 3/386* (2013.01); *C12Y 302/01017* (2013.01)

(58) Field of Classification Search
None
See application file for complete search history.

(56) References Cited

U.S. PATENT DOCUMENTS

| 2015/0342197 A1* | 12/2015 | King | A01N 43/90 424/94.2 |
| 2016/0038572 A1* | 2/2016 | Nelson | C12N 9/80 424/94.61 |
| 2017/0127683 A1* | 5/2017 | Schuch | A61K 38/164 |

FOREIGN PATENT DOCUMENTS

| KR | 10-1200333 B1 | 11/2012 |
| KR | 10-1596665 B1 | 2/2016 |
| KR | 10-1785487 B1 | 10/2017 |
| KR | 10-2017-0087770 A | 11/2017 |
| KR | 10-1818499 B1 | 1/2018 |
| KR | 10-2097128 B1 | 4/2020 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Hamed Haddad Kashani et al., "A Novel Chimeric Endolysin with Antibacterial Activity against Methicillin-Resistant *Staphylococcus aureus*", Frontiers in Cellular and Infection Microbiology, Jun. 30, 2017, pp. 1-12, vol. 7.
Bokyung Son et al., "KoSFoST Beyond 50 Years: Renew the New in Food Science", 2018 KoSFOST International Symposium and Annual Meeting, Jun. 27-29, 2018, 2 pgs.
Bokyung Son et al., "Viruses of Microbes 2018", EMBO Workshop, Jul. 9-13, 2018, 2pgs.
International Search Report for PCT/KR2020/005243 dated, Jul. 30, 2020 (PCT/ISA/210).

* cited by examiner

*Primary Examiner* — Christian L Fronda
(74) *Attorney, Agent, or Firm* — Sughrue Mion, PLLC (57) ABSTRACT

The present invention relates to chimeric endolysin Lys109 which effectively controls *Staphylococcus aureus*, wherein the endolysin Lys109 of the present invention has a novel amino acid sequence that has not been conventionally studied. Endolysin Lys109 of the present invention can be used as a biological regulator capable of effectively inhibiting a wide range of *Staphylococcus aureus* and a biofilm produced thereby. In addition, endolysin Lys109 can kill *Staphylococcus aureus* without regard for resistance to conventional antibiotics, and thus can be widely used for treatment of diseases caused by *Staphylococcus aureus* infection. Moreover, endolysin Lys109 can also be used to resolve medical problems caused by *Staphylococcus aureus* which has antibiotic resistance.

7 Claims, 5 Drawing Sheets
Specification includes a Sequence Listing.

CHIMERIC ENDOLYSIN LYS109 WITH ANTIMICROBIAL ACTIVITY AGAINST *STAPHYLOCOCCUS AUREUS*

CROSS REFERENCE TO RELATED APPLICATIONS

This application is a National Stage of International Application No. PCT/KR2020/005243, filed Apr. 21, 2020, claiming priority to Korean Patent Application No. 10-2019-0073058, filed Jun. 19, 2019, the entire disclosures of which are incorporated herein by reference.

TECHNICAL FIELD

The present invention relates to chimeric endolysin Lys109 effective in controlling *Staphylococcus aureus*, and more specifically, to chimeric endolysin Lys109, which exhibits sensitivity to *Staphylococcus aureus* and has excellent effects even in milk.

BACKGROUND ART

*Staphylococcus aureus* is a gram-positive bacterium, is a facultative anaerobe that does not form spores, and is mainly found in livestock feces, inflamed wounds, or cooking utensils that are frequently touched by humans. It infects humans and animals, leading to serious diseases such as postoperative infections, abscesses, endocarditis and toxic shock syndrome. In addition, *Staphylococcus aureus* produces highly heat-resistant toxins such as TSST-1, EF, alpha, beta, and delta toxins, and thus is not easily killed and may cause serious food poisoning.

In order to control *Staphylococcus aureus* having the characteristics described above, antibiotics have been mainly used to date. However, the widespread use of antibiotics has caused the problem of generation of bacteria that are resistant to antibiotics, such as methicillin-resistant *S. aureus*.

In an attempt to overcome this problem, the use of bacteriophages and bacteriophage-derived endolysins has recently emerged as an alternative. Bacteriophages, which are a kind of virus that specifically infects bacteria, are present in various environments on the earth, such as in food, soil, sewage and seawater, and the global population is estimated to be about $1 \times 10^{32}$. Bacteriophages are broadly classified into virulent phages that repeat only a lytic cycle, and temperate phages that undergo both a lytic cycle and a lysogenic cycle.

Phages in the lytic cycle produce 100 to 200 new phages about 30 minutes after bacterial infection, destroy the bacterial membrane, and lyse out of the bacteria. The growth rate of phages is much faster than that of bacteria, so they can act as a key factor in limiting the growth of bacteria. Weakly toxic phages insert genetic information of phages into the genome of the host bacterium, so the shape of phases disappears, but the host bacterium is not destroyed. This state lasts as long as the host bacteria are in good environmental conditions. When the environment of the host bacteria deteriorates, the cycle of some phage genes inserted into the genome of the host bacteria is converted to a lytic cycle, and new phages are produced, lyse the host bacteria, and are released from the host. For this reason, cases of successfully preventing and treating various diseases using toxic phages have been reported.

Meanwhile, an endolysin is an enzyme produced by bacteriophage to destroy the cell wall of peptidoglycan and is used when releasing virions out of the cell at the last stage of the lytic cycle of the bacteriophage. Endolysins rapidly kill bacteria at a low concentration and are considered to be a potential alternative for antibiotics since they do not facilitate the development of resistant bacteria.

Endolysins targeting *Staphylococcus aureus* are classified into 5 groups depending on the domain composition. However, there is a problem in that it is not easy to develop novel endolysins because the homology of the amino acid sequence in each group is high, that is, 90% or more, and thus genetic diversity is very low. In addition, endolysin targeting *Staphylococcus aureus* is difficult to overexpress in *E. coli*, and even if overexpressed, it is difficult to obtain soluble proteins. Therefore, there is an urgent need to develop a novel endolysin having excellent capability to control *Staphylococcus aureus* as an alternative to antibiotics.

DISCLOSURE

Technical Problem

Therefore, it is one object of the present invention to develop and provide a novel endolysin highly effective in controlling *Staphylococcus aureus* as an alternative to antibiotics.

Technical Solution

In accordance with the present invention, the above and other objects can be accomplished by the provision of endolysin Lys109 capable of lysing *Staphylococcus aureus* and controlling a *Staphylococcus aureus* biofilm, the endolysin Lys109 having an amino acid sequence of SEQ ID NO: 1.

In the endolysin Lys109 of the present invention, the *Staphylococcus aureus* is, for example, methicillin-resistant *S. aureus* (MRSA) or methicillin-sensitive *S. aureus* (MSSA).

In accordance with another aspect of the present invention, provided is a food composition containing the endolysin Lys109 having the amino acid sequence of SEQ ID NO: 1.

In accordance with another aspect of the present invention, provided is a pharmaceutical composition for preventing or treating *Staphylococcus aureus* infection containing the endolysin Lys109 having the amino acid sequence of SEQ ID NO: 1.

In the pharmaceutical composition, the *Staphylococcus aureus* is preferably methicillin-resistant *S. aureus* (MRSA) or methicillin-sensitive *S. aureus* (MSSA).

In accordance with another aspect of the present invention, provided is a feed composition containing the endolysin Lys109 having the amino acid sequence of SEQ ID NO: 1.

In accordance with another aspect of the present invention, provided is a detergent composition containing the endolysin Lys109 having the amino acid sequence of SEQ ID NO: 1.

Advantageous Effects

The endolysin Lys109 of the present invention is an endolysin having a novel amino acid sequence that has not been previously researched and can be utilized as a biological regulator capable of effectively inhibiting a wide range of varieties of *Staphylococcus aureus* and the biofilm produced by *Staphylococcus aureus*. In addition, the endolysin Lys109 can kill *Staphylococcus aureus* regardless of resistance to conventional antibiotics and thus can be used extensively for the treatment of diseases caused by *Staphylococcus aureus* infection. In addition, the endolysin Lys109 can also be used to solve medical problems caused by antibiotic-resistant *Staphylococcus aureus*.

DESCRIPTION OF DRAWINGS

A of FIG. 1 illustrates the domain configuration of endolysin Lys109, and B of FIG. 1 illustrates the result of protein purification of endolysin Lys109 (about 56 KDa).

BEST MODE

In one aspect, the present invention is directed to endolysin Lys109 capable of lysing *Staphylococcus aureus* and controlling a *Staphylococcus aureus* biofilm, the endolysin Lys109 having the amino acid sequence of SEQ ID NO: 1.

Figure 1:
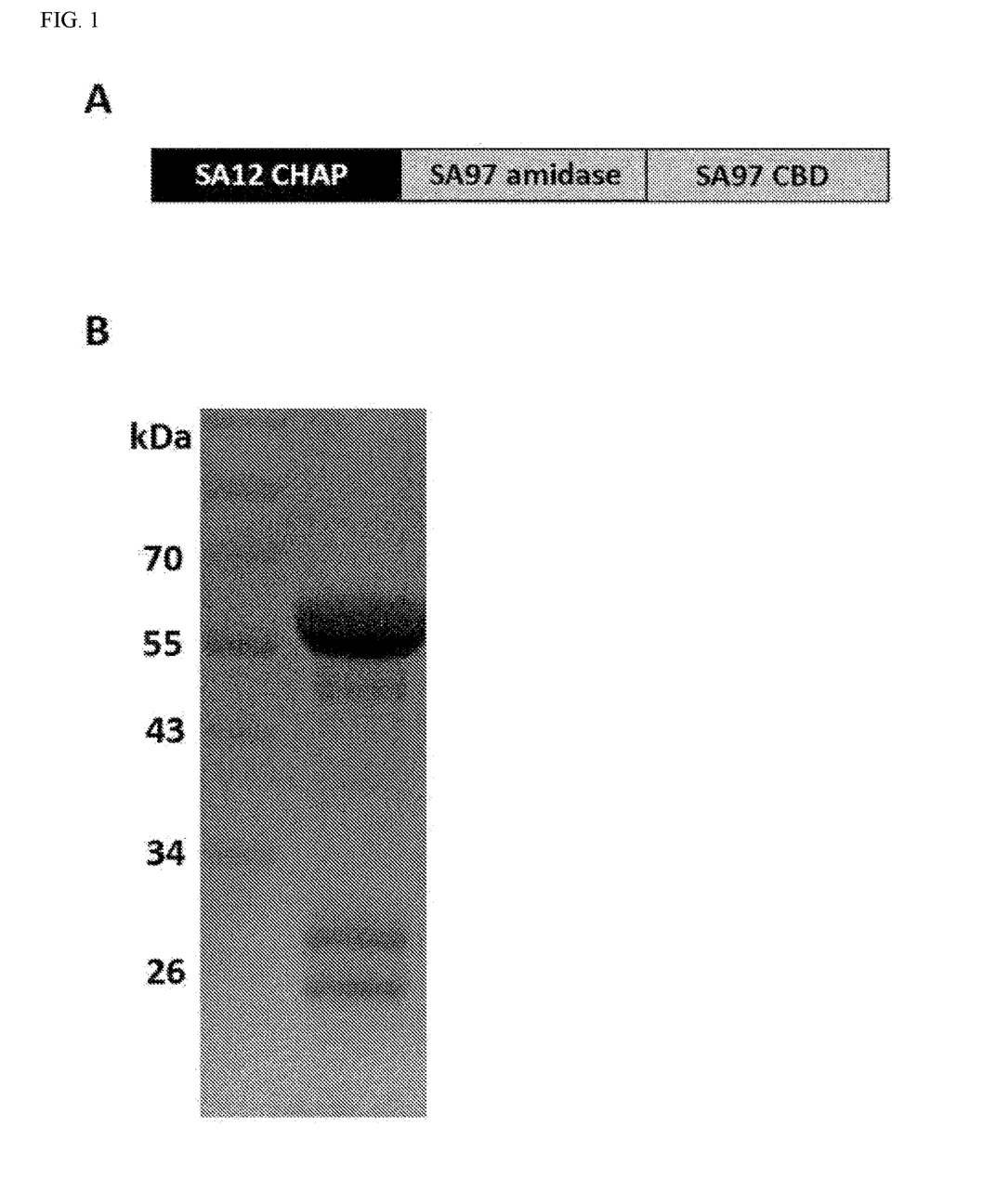

The present inventors developed chimeric endolysin Lys109 consisting of a LysSA12 CHAP domain, and LysSA97 amidase and CBD (cell-binding domain), as can be seen from FIG. 1, by engineering endolysin using a random domain-swapping method.

The result of investigation of the nucleotide sequence homology of the chimeric endolysin Lys109 developed in the present invention using BlastN and BlastP programs showed that the chimeric endolysin Lys109 had a homology of 78% with the endolysin of the bacteriophage StauST398-1 and 80% with the endolysin of bacteriophage ΦB166 and ΦB236.

Meanwhile, in the endolysin Lys109 of the present invention, the *Staphylococcus aureus* is, for example, methicillin-resistant *S. aureus* (MRSA) or methicillin-sensitive *S. aureus* (MSSA). In the following experiment performed with *Staphylococcus aureus* as a host, the endolysin of the present invention formed plaques to lyse *Staphylococcus aureus*. In particular, through the experimentation described below it was demonstrated that the endolysin of the present invention was able to kill *Staphylococcus aureus*, including methicillin-resistant *Staphylococcus aureus*, within a short time even when using a small amount, and exhibited higher *Staphylococcus aureus* lytic activity in milk than other known endolysins.

Meanwhile, mucus, which is a colony of bacteria covered with a polymer substrate, may often be present in an area infected with bacteria. The mucous bacterial complex formed by bacteria is called a "biofilm". That is, the biofilm is a complex composed of a bacterial colony, which is a solid biological surface, and an outer membrane, which is a non-biological surface. Therefore, in the present specification, the term "biofilm" is defined to mean the entirety including an outer membrane and bacterial colonies contained therein.

A biofilm can be thought of as a small city composed of bacteria, in which the bacteria communicate with one another and defend themselves against foreign matter. Based thereon, the biofilm enables bacteria to survive various environmental stresses including antibiotics.

Meanwhile, antibiotics effective against individually suspended planktonic bacteria also tend to lose efficacy when the bacteria form a biofilm. When bacteria form a biofilm, antibodies and the like cannot penetrate the outer membrane present in the biofilm, so the resistance of bacteria to antibiotics can be increased about 1,000 times, and the host immune system may be inactivated (incapacitated). For these reasons, when a biofilm is formed, the activity of antibiotics, which are widely used to treat infections, is inhibited, and as a result, the therapeutic effect of antibiotics is weakened.

The formation of a biofilm indicates a state of chronic bacterial infection. In this case, as described above, the susceptibility of bacteria to antibiotics is low, so even the use of antibiotics has little effect. That is, in order to overcome this, simply overprescribing antibiotics will only increase the antibiotic resistance of bacteria. That is, using only antibiotics to treat a bacterial infection is ineffective after a biofilm is formed. In particular, the infection by the bacteria forming the biofilm is often caused by multiple-drug-resistant bacteria that are resistance to several antibiotics, which aggravates the problem.

In order to prevent the ineffectiveness of antibiotic treatment due to the formation of a biofilm, it is necessary to develop a novel antibiotic that can remove a biofilm when the same is formed, or to use an ingredient that can destroy the outer membrane present in the biofilm along with existing antibiotics to allow the existing antibiotics to exert the efficacy thereof. However, the endolysin Lys109 of the present invention is very efficient because it can effectively remove the *Staphylococcus aureus* biofilm formed in polystyrene, and can kill only *Staphylococcus aureus* regardless of resistance to existing antibiotics.

Meanwhile, the present invention provides a food composition containing the endolysin Lys109 having the amino acid sequence of SEQ ID NO: 1, and the endolysin Lys109 of the present invention is used to remove *Staphylococcus aureus*, which is a big obstacle in food-processing and distribution processes, and a biofilm formed thereby.

The food composition of the present invention is preferably added to any one selected from meat, grains, caffeinated beverages, general beverages, chocolate, bread, snacks, confectioneries, pizza, jellies, noodles, gum, ice cream, alcoholic beverages, alcohol, vitamin complexes and other health supplements, but is not necessarily limited thereto. The endolysin Lys109 of the present invention is preferably present in an amount of 0.1 to 20% by weight of all food constituents. When the endolysin Lys109 is present in an amount less than 0.1% by weight, the effect is insignificant, and when the amount thereof exceeds 20% by weight, the increase in the effect compared to the amount used is insignificant, which is uneconomical.

Meanwhile, the present invention provides a pharmaceutical composition for preventing or treating *Staphylococcus aureus* infection containing the endolysin Lys109 having the amino acid sequence of SEQ ID NO: 1. In this case, the *Staphylococcus aureus* is preferably methicillin-resistant *S. aureus* (MRSA) or methicillin-sensitive *S. aureus* (MSSA). The endolysin Lys109 of the present invention can be used to prevent diseases caused by *Staphylococcus aureus* or the biofilm formed thereby, or to treat diseases caused by *Staphylococcus aureus* or the biofilm formed thereby.

The endolysin Lys109 contained in the pharmaceutical composition of the present invention can specifically kill *Staphylococcus aureus* and effectively remove the biofilm formed thereby, as described above, and thus can be effective for the treatment of various diseases, for example mastitis, dermatitis, sepsis, purulent diseases, food poisoning, pneumonia, osteomyelitis, impetigo, bacteremia, endocarditis, and enteritis, which are caused by *Staphylococcus aureus* and have become chronic due to the biofilm formed thereby. The composition for this purpose may further contain other ingredients having previously demonstrated antibacterial activity against *Staphylococcus aureus* in order to obtain an additional therapeutic effect.

The content of endolysin Lys109 contained in the pharmaceutical composition of the present invention is preferably adjusted depending on the method of use and the condition of the user. The content of endolysin Lys109 in the pharmaceutical composition of the present invention may be 0.000001 to 5% by weight compared to the pharmaceutical composition, but is not necessarily limited thereto. The pharmaceutical composition of the present invention may further contain a pharmaceutically acceptable carrier, diluent, or excipient, in addition to the active ingredient. Examples of usable carriers, excipients, or diluents include lactose, dextrose, sucrose, sorbitol, mannitol, xylitol, erythritol, maltitol, starch, acacia gum, alginate, gelatin, calcium phosphate, calcium sulfate, cellulose, methyl cellulose, microcrystalline cellulose, polyvinylpyrrolidone, water, methylhydroxybenzoate, propylhydroxybenzoate, talc, magnesium stearate and minerals, and combinations thereof. In addition, fillers, anti-aggregants, lubricants, wetting agents, fragrances, emulsifiers, preservatives and the like may be further contained when the prophylactic and therapeutic agents are pharmaceuticals.

Meanwhile, the formulation of the pharmaceutical composition of the present invention may be provided in a suitable form depending on the method of use, and is particularly prepared by adopting a method known in the art to provide rapid, sustained or delayed release of the active ingredient after administration to mammals. Specifically, the formulation, for example, includes any one selected from plasters, granules, lotions, liniments, lemonades, aromatic waters, powders, syrups, ophthalmic ointments, liquids formulations, aerosols, extracts, elixirs, ointments, fluid extracts, emulsions, suspensions, decoctions, infusions, eye drops, tablets, suppositories, injections, spirits, cataplasma, capsules, creams, troches, tinctures, pastas, pills, and soft or hard gelatin capsules.

Meanwhile, the dosage of the pharmaceutical composition of the present invention is preferably determined in consideration of the administration method and the age, gender, and weight of the user. For example, the pharmaceutical composition may be administered at least once daily at 0.001 to 100 mg/kg (body weight) based on the active ingredient. However, the dosage is provided only as an example for illustration, and may be changed depending on the condition of the user.

Meanwhile, the present invention provides a feed composition containing the endolysin Lys109 having the amino acid sequence of SEQ ID NO: 1. The feed composition may contain the endolysin Lys109 in an amount of 0.000001 to 1.0% by weight, based on the total weight. The feed composition of the present invention is mixed with a conventional feed composition and fed by oral administration, and has almost no problem of tolerance or side effects such as immunosuppression even when continuously administered or administered in excess.

Meanwhile, the present invention provides a detergent composition containing the endolysin Lys109 consisting of the amino acid sequence of SEQ ID NO: 1. The detergent composition of the present invention may further contain ingredients commonly used in detergent compositions, for example, conventional adjuvants such as stabilizers, solubilizers and fragrances, and carriers. When the formulation of the cleaning composition of the present invention is a paste, cream, or gel, a carrier ingredient such as animal oil, vegetable oil, wax, paraffin, starch, tragacanth, cellulose derivatives, polyethylene glycol, silicone, bentonite, silica, talc, zinc oxide, etc. may be used.

When the formulation of the detergent composition of the present invention is a solution or emulsion, a solvent, solubilizer or emulsifier is used as a carrier component, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

When the formulation of the detergent composition of the present invention is a suspension, as a carrier component, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, or tragacanth may be used.

When the formulation of the detergent composition of the present invention is a spray, lactose, talc, silica, aluminum hydroxide, calcium silicate or polyamide powder may be used as a carrier ingredient, and in particular, the spray may further contain propellants such as chlorofluorohydrocarbon, propane/butane or dimethyl ether.

When the formulation of the detergent composition of the present invention is a surfactant-containing cleansing agent, as carrier components, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, fatty alcohol, fatty acid glyceride, fatty acid diethanolamide, vegetable oil, lanolin derivatives, ethoxylated glycerol fatty acid ester and the like can be used.

When the detergent of the present invention is used as a medical detergent, it may be provided as a spray which is applied to a part to prevent biofilm formation, such as an artificial joint, a catheter surface, an endoscope, or a wound. In addition, the detergent of the present invention can also be used for cleaning by ultrasonic cleaners and automatic cleaners. Here, a method of immersing the medical device in the detergent of the present invention is also possible.

The detergent composition of the present invention is useful as a disinfectant for kitchens and cooking equipment.

The effective dose of endolysin Lys109 in general detergents and medical detergents used in the present invention may be easily determined through simple preliminary investigation by those skilled in the art, and will depend on the field of application and the application method. Preferably, the endolysin Lys109 may be present in an amount of 0.001% (w/v) to 0.1% (w/v).

MODE FOR INVENTION

Hereinafter, the present invention will be described in more detail with reference to the following examples and experimental examples, but the scope of the present invention is not limited to the examples and experimental examples, and includes variations and technical concepts equivalent thereto.

Example 1: Obtained Chimeric Endolysin Lys109 of Present Invention (1) Endolysin Engineering Using Random Domain-swapping Method In order to transform *Escherichia coli* BL21 (DE3) with two vectors having different types of promoters, four CHAP domain genes (obtained from LysSA11, LysSA12, LysSAP4, and LysSA97) and three amidase domain genes (obtained from LysSA12, LysSAP4 and LysSA97) were randomly ligated to pET28a vectors containing four different CBD genes (obtained from LysSA11, LysSA12, LysSAP4 and LysSA97), followed by transformation. Then, a gene encoding SPN1S, a protein that lyses *E. coli* in cells, was bound to the pBAD33 vector, and *E. coli* was transformed with this vector as well.

When *Escherichia coli* was broken through the SPN1S protein, an endolysin expressed therein was released and reacted with the host bacterium, *S. aureus*, to form a clear zone. More specifically, expression of new endolysin of each clone was commenced by IPTG in a 96-well plate and then an SPN1S protein was expressed through the addition of arabinose. The new endolysin was screened by dotting 5 µl of the culture on a solid medium overlaid with *Staphylococcus aureus* cells and identifying the lysate generated after culture.

(2) Identification and Isolation of Endolysin Lys109

As a result of the screening, a chimeric endolysin that included unengineered endolysin and formed about 20 clear zones was obtained, a domain combination of endolysin was analyzed through sequence analysis, and Lys109 having the highest activity among them was obtained (A of FIG. 1).

Meanwhile, expression of Lys109 cloned into the pET-28a vector was induced by the addition of 0.5 mM IPTG. Then, the cell wall of the strain was removed, the residue was centrifuged, and the supernatant was passed through a Ni-NTA Superflow column to obtain pure chimeric endolysin Lys109 (B of FIG. 1). A of FIG. 1 illustrates the domain configuration of endolysin Lys109, and B of FIG. 1 illustrates the results of protein purification performed on endolysin Lys109 (about 56 KDa). The endolysin Lys109 has the amino acid sequence of SEQ ID NO: 1, and is encoded by the nucleotide sequence of SEQ ID NO: 2.

Example 2: Characterization of Endolysin Lys109 of Present Invention (1) Host Lytic Activity of Endolysin Lys109

Figure 2:
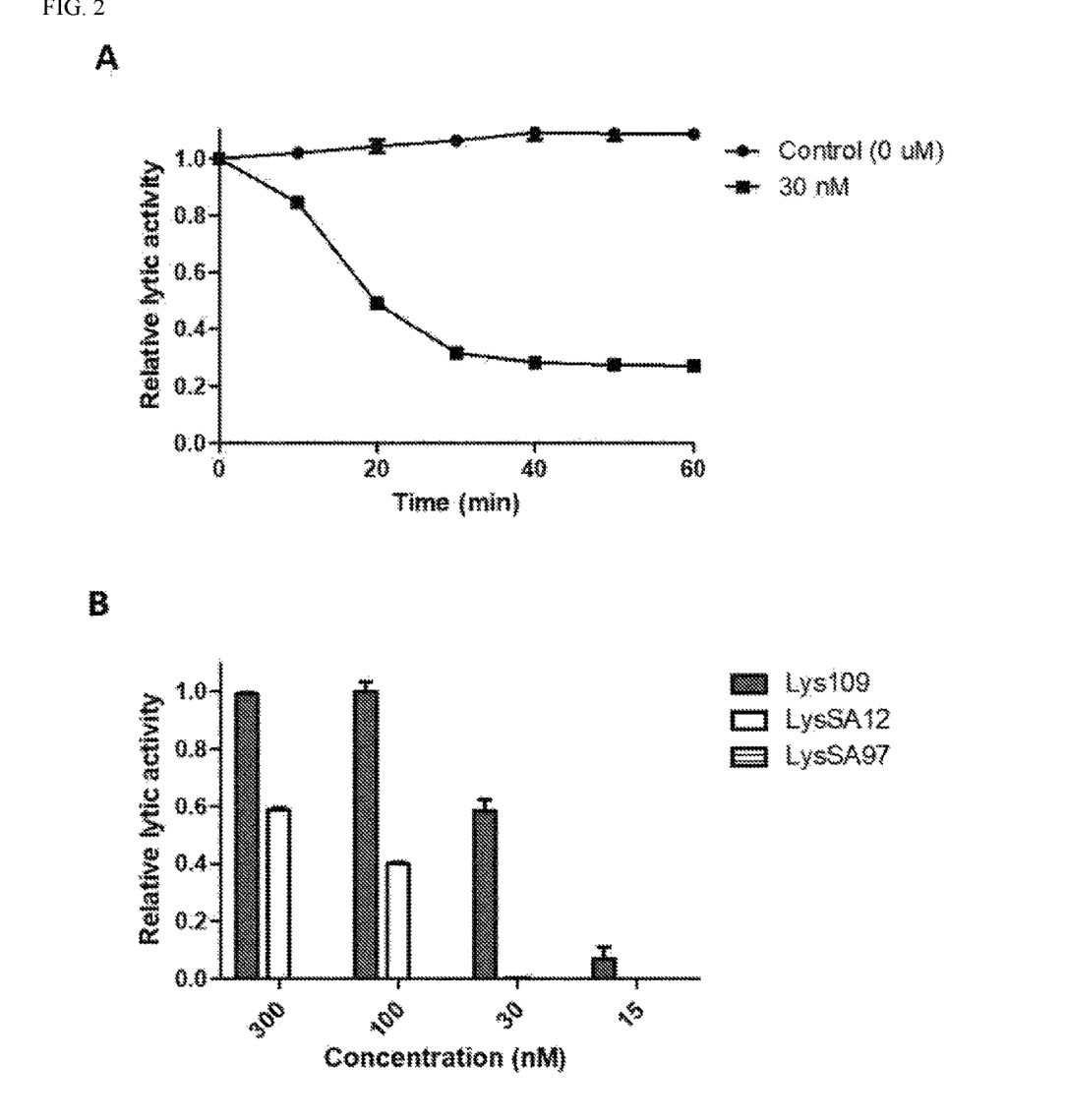
FIG. 2 illustrates the result of identifying the effect of the endolysin Lys109 of the present invention on killing *Staphylococcus aureus*, more specifically, A of FIG. 2 illustrates the result of a comparison between a control group added only with a buffer and an experimental group treated with endolysin Lys109 of the present invention, and B of FIG. 2 illustrates the result of a comparison between endolysin Lys109 of the present invention and the parent endolysins LysSA12 and LysSA97 at different treatment concentrations.

The *Staphylococcus aureus* CCARM 3090 culture medium in the stationary phase stage was treated with 30 nM endolysin Lys109 isolated in Example 1, and as a result of the experiment, the absorbance was effectively reduced compared to a control group added only with a buffer (A of FIG. 2). In addition, when the endolysin Lys109 was added at different concentrations, it exhibited a concentration-dependent decrease in absorbance and remarkably higher lytic activity compared to the parent endolysins LysSA12 and LysSA97 (B of FIG. 2). FIG. 2 illustrates the result identifying the effect of killing *Staphylococcus aureus* of endolysin Lys109 of the present invention.

The above results proved that the endolysin Lys109 according to the present invention did not simply inhibit the growth of the susceptible strain, but lysed the strain, and more effectively controlled the susceptible strain than the parental endolysins, even at low concentrations.

Figure 3:
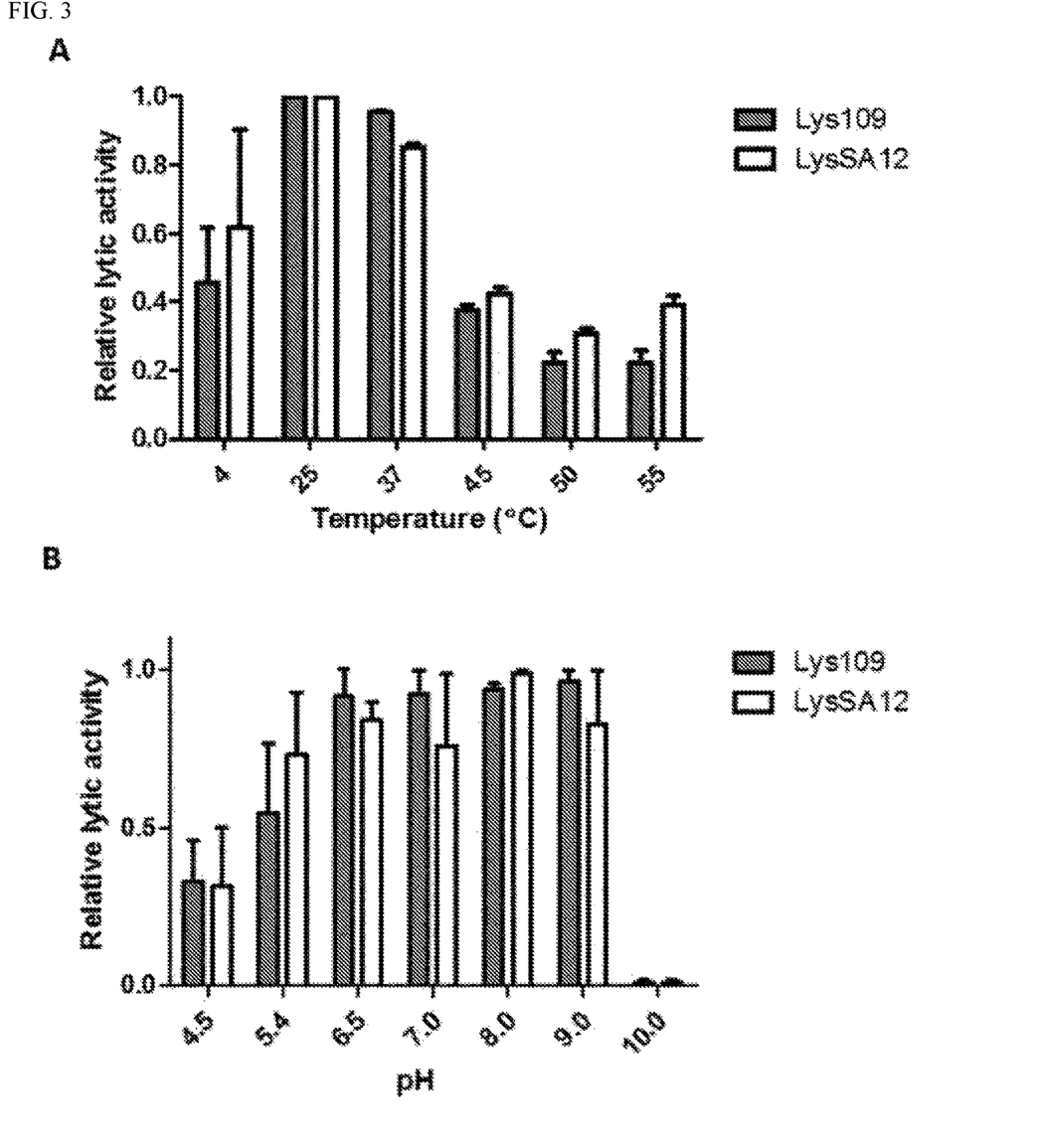
FIG. 3 illustrates the result of identifying the effects of pH and heat on the *Staphylococcus aureus* lytic activity of endolysin Lys109, more specifically, A of FIG. 3 illustrates an experimental result for pH, and B of FIG. 3 illustrates an experimental result for heat.

(2) Conditions Under which Endolysin Lys109 Exhibits Effective Antibacterial Activity The antibacterial activity of the endolysin Lys109 of the present invention was stable in the basic range from pH 6.5 to 9.0 (A of FIG. 3). In addition, the endolysin Lys109 was active at 25 to 55° C. and exhibited the most effective antibacterial activity at 25 to 37° C. (B of FIG. 3). FIG. 3 illustrates the result of identifying the effects of pH and heat on the *Staphylococcus aureus* lytic activity of endolysin Lys109.

(3) Antibacterial Activity Range of Endolysin Lys109

The sensitivity of endolysin Lys109 to various bacteria was determined, and is shown in Table 1 below.

TABLE 1

Determination of sensitivity of endolysin Lys109

| Species | Strains | LysSA12 (pmol) 167 | LysSA12 (pmol) 16.7 | Lys109 (pmol) 167 | Lys109 (pmol) 16.7 |
|---|---|---|---|---|---|
| S. aureus | Human isolate 117 | + | − | ++ | + |
|  | Human isolate 119 | + | − | ++ | − |
|  | Animal isolate 154 | + | − | ++ | − |
|  | Animal isolate 134 | + | − | ++ | − |
|  | Clinical isolate 1163 | + | − | ++ | − |
|  | Clinical isolate FMB1 | + | − | ++ | − |
|  | Mastitis cow milk isolate | ++ | − | ++ | + |
|  | ATCC 23235 | + | − | ++ | + |
|  | ATCC 13301 | + | − | ++ | − |
|  | CCARM 3090 | + | − | ++ | − |
| S. hominis | ATCC 37844 | + | − | ++ | + |
| S. saprophyticus | ATCC 15305 | + | − | ++ | + |
| S. haemolyticus | ATCC 29970 | + | − | ++ | − |
| S. capitis | ATCC 35661 | + | − | ++ | − |
| Bacillus cereus | KCCM 40133 | − | − | − | − |
| B. subtilis | 168 | − | − | − | − |
| Streptococcus thermophilus | ATCC 19258 | − | − | − | − |

As a result of the experiment, the endolysin Lys109 exhibited strong activity against various *Staphylococcus aureus*, including methicillin-resistant *Staphylococcus aureus* strains. However, the endolysin Lys109 could not kill gram-positive bacteria. The above results showed that the Lys109 endolysin of the present invention has a wide range of antibacterial activity against *Staphylococcus aureus*.

Example 3: Confirmation of Biofilm Control Ability of Endolysin Lys109 of Present Invention In order to examine the biofilm removal activity of the endolysin Lys109 of the present invention by targeting *Staphylococcus aureus* RN4220 that produces a biofilm, *Staphylococcus aureus* was cultured overnight in TSB medium containing 0.25% D-(+)-glucose.

Figure 4:
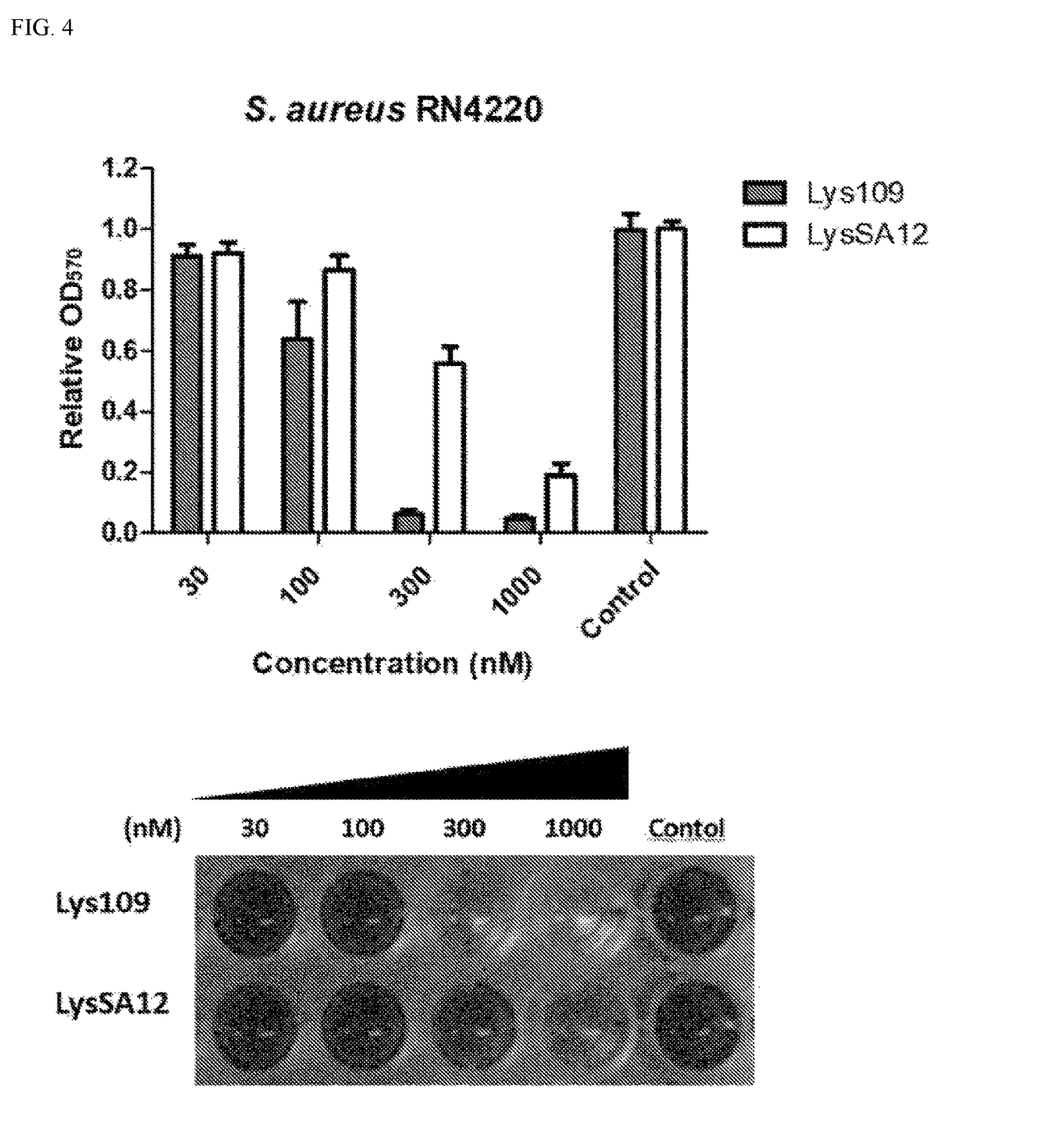
FIG. 4 illustrates the result of identifying the biofilm removal ability of the endolysin Lys109 of the present invention.

The culture solution of the *Staphylococcus aureus* was diluted 1:100 using a TSB medium containing D-(+)-glucose, and 200 µl thereof was seeded into each well of a 96-well plate. Then, the culture was stationarily cultured at 37° C. for 24 hours. After 24-hours culture, the result was washed three times with 200 µl of phosphate-buffered saline and a solution containing endolysin and a solution not containing endolysin were added to the wells, followed by stationary culture at 37° C. for 24 hours. Then, the medium was removed and each well was washed once with phosphate-buffered saline. Then, each well was stained with 200 µl of 1% crystal violet and then washed 3 times with phosphate-buffered saline. The biofilm was eluted with 33% acetic acid and the absorbance ($OD_{570}$) of the eluted solution was measured to determine the degree of removal of the biofilm (FIG. 4). FIG. 4 illustrates the result of identifying the biofilm removal ability of the endolysin Lys109 of the present invention.

The result of the experiment showed that endolysin Lys109 effectively removed the *Staphylococcus aureus* biofilm formed inside the well.

Example 4: Measurement of Lytic Activity of Endolysin Lys109 in Milk

Figure 5:
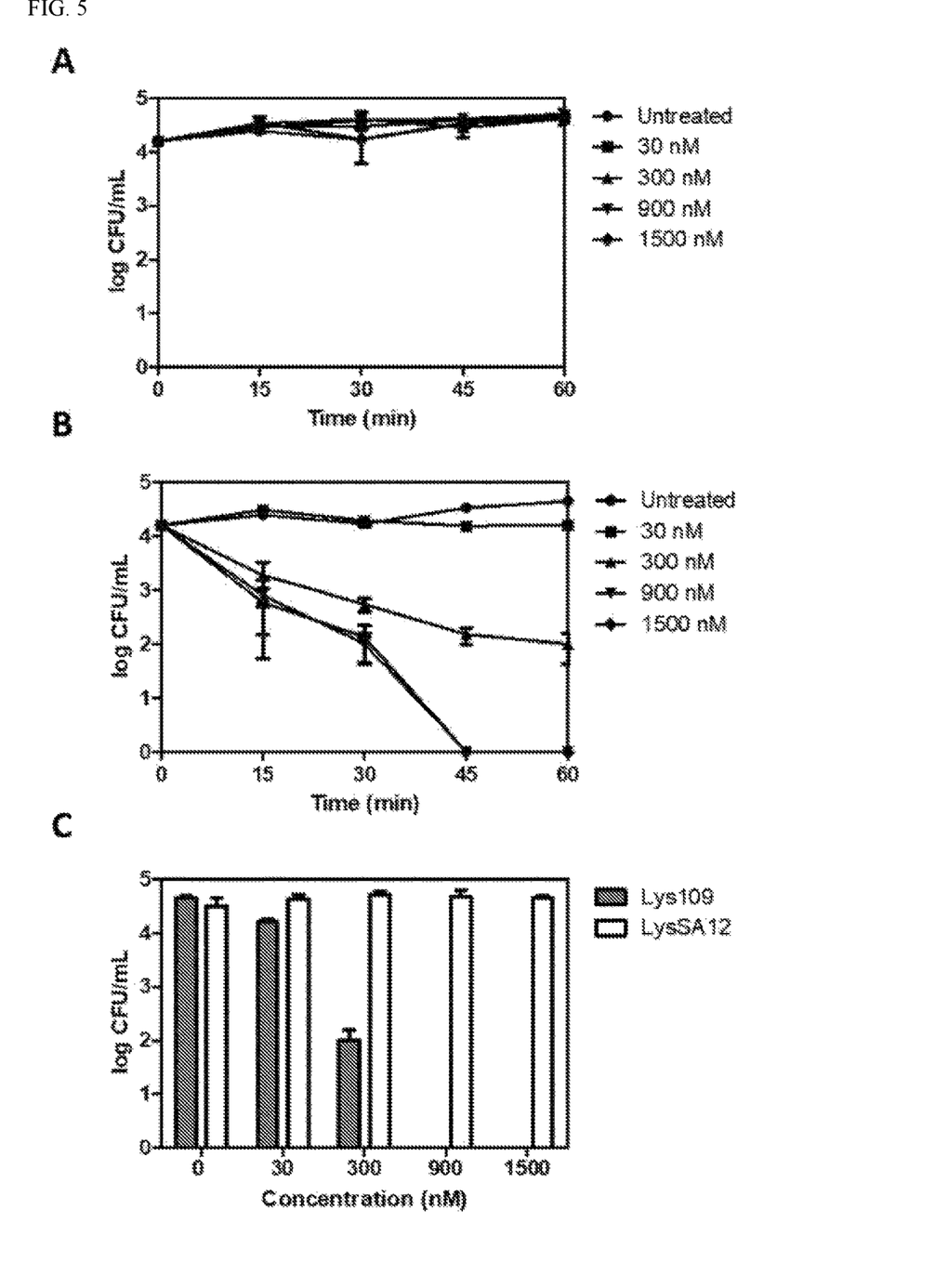
FIG. 5 illustrates the result of measuring the bactericidal effect after treating milk (dairy product) with endolysin Lys109. More specifically, A of FIG. 5 illustrates the result of treatment with endolysin LysSA12, B of FIG. 5 illustrates the result of treatment with endolysin Lys109 of the present invention, and C of FIG. 5 illustrates the result of a comparison therebetween.

After treating dairy products reported to frequently cause food poisoning by *Staphylococcus aureus* with endolysin Lys109, the bactericidal effect was measured. While commercially available milk S was stored at room temperature (25° C.), the effect of endolysin Lys109 was determined. The dairy product was contaminated with *Staphylococcus aureus* in an amount of about $10^3$ CFU/ml, and the result of treatment with endolysin Lys109 showed that *Staphylococcus aureus* was not detected within 1 hour at room temperature (25° C.) (FIG. 5). FIG. 5 illustrates the result of measuring the bactericidal effect of treating milk (dairy product) with endolysin Lys109. In FIG. 5, A illustrates the result of treatment with endolysin LysSA12, B illustrates the result of treatment with the endolysin Lys109 of the present invention, and C illustrates the result of a comparison therebetween.

The above results proved that the endolysin Lys109 of the present invention can be used as a novel antibacterial substance that can replace antibiotics.

---

The invention claimed is:

1. Endolysin Lys109 capable of lysing *Staphylococcus aureus*, the endolysin Lys109 having the amino acid sequence of SEQ ID NO: 1.

2. The endolysin Lys109 according to claim 1, wherein the *Staphylococcus aureus* is methicillin-resistant *S. aureus* (MRSA) or methicillin-sensitive *S. aureus* (MSSA).

3. A food composition comprising the endolysin Lys109 of claim 1.

4. A composition for treating *Staphylococcus aureus* infection comprising the endolysin Lys109 of claim 1.

5. The composition according to claim 4, wherein the *Staphylococcus aureus* is methicillin-resistant *S. aureus* (MRSA) or methicillin-sensitive *S. aureus* (MSSA).

6. A feed composition comprising the endolysin Lys109 of claim 1.

7. A detergent composition comprising the endolysin Lys109 of claim 1.

* * * * *

SEQUENCE LISTING

```
<160> NUMBER OF SEQ ID NOS: 2

<210> SEQ ID NO 1
<211> LENGTH: 476
<212> TYPE: PRT
<213> ORGANISM: Artificial Sequence
<220> FEATURE:
<223> OTHER INFORMATION: Lys109

<400> SEQUENCE: 1

Met Gln Ala Lys Leu Thr Lys Lys Glu Phe Ile Glu Trp Leu Lys Thr
 1               5                  10                  15

Ser Glu Gly Lys Gln Tyr Asn Ala Asp Gly Trp Tyr Gly Phe Gln Cys
                20                  25                  30

Phe Asp Tyr Ala Asn Ala Gly Trp Gln Val Leu Phe Gly Tyr Asn Leu
            35                  40                  45

Lys Gly Val Gly Ala Lys Asp Ile Pro Ser Ala Asn Asp Phe Asn Gly
    50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
            100                 105                 110

Asn Trp Leu Gly Gly Gly Trp Thr Asp Gly Val Gln Gln Pro Gly Ser
        115                 120                 125

Gly Trp Glu Lys Val Thr Arg Arg Gln His Ala Tyr Asp Phe Pro Met
    130                 135                 140

Trp Phe Ile Arg Pro Asn Phe Lys Ser Glu Thr Ala Pro Arg Ser Leu
145                 150                 155                 160

Glu Gln Asp Lys Leu Ser Lys Gly Lys Lys Ile Met Leu Val Ala Gly
                165                 170                 175

His Gly Ile Gly Ala Tyr Ser Asn Asp Pro Gly Ala Val Ala Asn Gly
            180                 185                 190

Glu Asn Glu Arg Asp Phe Asn Arg Lys Asn Ile Ile Pro Arg Val Lys
        195                 200                 205
```

```
Lys Tyr Leu Glu Ser Val Gly Asn Thr Val Leu Leu Tyr Gly Gly Asn
    210                 215                 220

Ser Met Asn Gln Asp Leu Tyr Gln Asp Thr Leu Tyr Gly Gln Arg Val
225                 230                 235                 240

Gly Asn Tyr Lys Asp Tyr Gly Met Tyr Trp Ile Lys Ser Glu Val Lys
                245                 250                 255

Pro Asp Ala Ile Ile Glu Phe His Leu Asp Ser Ala Ser Pro Gln Ala
                260                 265                 270

Ser Gly Gly His Val Ile Ile Ser Asp Arg Phe Pro Ala Asp Asp Ile
                275                 280                 285

Asp Lys Ala Leu Ser Ser Ala Leu Asp Lys Val Gly Lys Ile Arg
290                 295                 300

Gly Val Thr Pro Arg Gly Asp Leu Leu Asn Ala Asn Val Ser Ala Asp
305                 310                 315                 320

Leu Asn Leu Asn Tyr Arg Leu Ile Glu Leu Gly Phe Ile Thr Ser Thr
                325                 330                 335

Lys Asp Leu Asn Tyr Ile Lys Asn Asn Leu Asp Ser Phe Thr Lys Arg
                340                 345                 350

Ile Ala Glu Ala Ile Asn Gly Arg Gln Ile Asp Ala Pro Ser Ser Gly
                355                 360                 365

Ser Glu Phe Ser Ser Lys Pro Ser Ala Asp Lys Ile Thr Trp Asn Trp
370                 375                 380

Lys Gly Val Phe Tyr Pro Asn Pro Glu Lys Ala Ile Arg Val Arg Lys
385                 390                 395                 400

Thr Ala Gly Leu Thr Gly Thr Val Val Glu Glu Asp Ser Trp Leu Tyr
                405                 410                 415

Thr Lys Asp Asp Trp Val Lys Phe Asp Gln Val Ile Lys Lys Asp Gly
                420                 425                 430

Tyr Trp Trp Ile Arg Phe Lys Tyr Gln Arg Glu Gly Ser Ser Thr Asn
                435                 440                 445

Asn Phe Tyr Cys Ala Val Cys Arg Ile Thr Asp Lys Glu Gln Lys Ile
                450                 455                 460

Lys Asn Glu Lys Tyr Trp Gly Thr Ile Glu Trp Ala
465                 470                 475

<210> SEQ ID NO 2
<211> LENGTH: 1431
<212> TYPE: DNA
<213> ORGANISM: Artificial Sequence
<220> FEATURE:
<223> OTHER INFORMATION: Lys109

<400> SEQUENCE: 2
atgcaagcaa aactaactaa aaaagagttt atagagtggt tgaaaacatc tgagggaaaa      60
caatataatg cggacggatg gtatggattt caatgctttg actatgccaa tgcaggttgg     120
caagtcttat ttggctacaa cttaaaaggt gtaggtgcca agacatccc aagtgctaat      180 gattttaacg gactagctac tgtataccaa aatacaccag acttcttagc gcaacctggc     240
gacatggttg tattcggtag taattatggt gcaggatacg gtcatgttgc atgggtaatt     300
gaagcaactt tagattatat cattgtatat gagcagaatt ggctcggcgg tggctggaca     360
gacggtgtac aacaacctgg ctctggttgg gaaaaagtta caagacgcca acacgcttac     420
gacttcccta tgtggtttat ccgtcctaac ttcaaaagcg aaacagctcc acgatcactc     480
gagcaagata agttatcaaa aggtaaaaaa atcatgcttg ggctggtca tggtattggt     540
```

```
gcatactcta acgacccagg tgccgttgcg aatggagaaa acgaaagaga ttttaaccgt    600
aaaaatatta tacctagagt gaaaaagtat cttgagtcag taggcaacac agtattgtta    660
tacggtggca actcgatgaa tcaagattta tatcaagata cattgtacgg tcaacgtgtt    720
ggaaactata aagattatgg catgtactgg attaaaagtg aagtcaaacc ggatgcaatc    780
atagagtttc atttagattc tgctagccca caagcaagtg gcgggcatgt aatcattagc    840
gatcgtttcc cagctgatga cattgacaag gcattaagta gtgcattaga taaaacagtg    900
ggtaaaataa gaggtgtgac acctagaggg gatttattga acgctaacgt gtctgctgat    960
cttaatctta attatcgttt aatcgaatta ggttttatca catctacgaa agatttaaac   1020
tacattaaaa acaatttaga cagcttcacg aagcggattg ctgaagccat taacggcaga   1080
caaattgatg cgccaagtag tggatccgaa tccagtagta agccaagcgc tgacaaaata   1140
acatggaatt ggaaaggcgt atttatcct aatccagaaa aagctataag agtcagaaaa    1200
acagctggat taaccggcac agtcgttgaa gaagattcat ggctatacac aaaagatgat   1260
tgggtaaaat tcgaccaagt cattaaaaaa gatggctact ggtggattag attcaaatat   1320
caacgtgagg gctctagtac taacaatttc tattgtgcag tgtgtagaat tactgataag   1380
gaacaaaaga ttaaaaatga aaaatattgg ggcacgattg agtgggctta a            1431
```